United States Patent [19]

Alt et al.

[11] Patent Number: 5,210,352
[45] Date of Patent: May 11, 1993

[54] FLUORENE COMPOUNDS

[75] Inventors: Helmut G. Alt; Syriac J. Palackal, both of Bayreuth, Fed. Rep. of Germany

[73] Assignee: Phillips Petroleum Company, Bartlesville, Okla.

[21] Appl. No.: 705,863

[22] Filed: May 28, 1991

Related U.S. Application Data

[63] Continuation-in-part of Ser. No. 697,363, May 9, 1991, Pat. No. 5,191,132.

[51] Int. Cl.$^5$ ................................................ C07C 1/20
[52] U.S. Cl. ...................................... 585/375; 585/317
[58] Field of Search ................ 585/360, 375; 562/405, 562/418, 460; 568/314, 809

[56] References Cited

U.S. PATENT DOCUMENTS 2,427,337  9/1947  Abbott, Jr. et al. ................. 250/669
3,426,069  2/1969  Fritz et al. ........................... 260/562

OTHER PUBLICATIONS

Ong, B. S. et al: 'Synthesis and Molecular Properties of 2-alkyl-4,5,7-trinitro fluoren-9-ones'. Chemistry and Industry (London), vol. 3, 1984, pp. 110-111.
Fieser et al: "Cholanthrene and Related Hydrocarbons" Jour. Amer. Chem. Soc., 57, 2174-2176 (1935).
Morrison et al: "Organic Chemistry", 4th Ed., 1983, pp. 742, 749, 753, 754.
Todd: "The Wolfe-Kishner Reaction", Organic Reactions, vol. IV, 1949, p. 386.
Barton et al: "Comprehensive Organic Chemistry", 1979, pp. 643-645.
Brewster et al: "Hydrogenolyses with Chloroaluminum hydrides", Jour. Org. Chem., 1964, 29, pp. 121-123.
Sawicki et al, J. Organic Chemistry 21, 243 (1956).
Huntress et al, J. Am. Chem. Soc. 64, 2845-2849 (1942).
Ghatak et al, Tetrahedron 24, 1577-1593.
Orchin et al, J. Am. Chem. Soc. 67, 122-124 (1945).

*Primary Examiner*—Asok Pal
*Assistant Examiner*—P. Achutamurthy
*Attorney, Agent, or Firm*—Edward L. Bowman

[57] ABSTRACT

New fluorene derivatives and new methods for forming fluorene derivatives are disclosed. Examples include processes for preparing tert-butyl substituted fluorenes, 1-methyl fluorene, and 4-methyl fluorene.

8 Claims, No Drawings

FLUORENE COMPOUNDS

This is a continuation-in part of application Ser. No. 07/697,363 filed May 9, 1991, now U.S. Pat. No. 5,191,132 the disclosure of which is incorporated herein by reference.

FIELD OF THE INVENTION

The present invention relates to fluorene compounds. In another aspect, the invention relates to methods for preparing various fluorene compounds.

BACKGROUND OF THE INVENTION

The term "fluorene" as used herein refers to the tricyclic compound which is generally illustrated by the following structural formula:

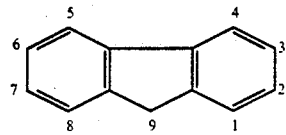

In the chemical names used herein, the position of substituents on the fluorene will be indicated by referring to the point of attachment on the ring carbon by the number system illustrated in the above formula. Unless otherwise indicated the term "fluorenyl" as used herein refers to the 9-fluorenyl radical.

A wide range of utilities have been disclosed for fluorene and various derivatives of fluorene. U.S. Pat. No. 4,016,289 discloses that certain fluorene derivatives are useful in preparing medicines for use in the treatment of viral diseases. U.S. Pat. No. 3,426,069 discloses that certain N-alkanoyl amino alkyl fluorene derivatives are useful as monomers for forming polyamides, polyureas, and the like. U.S. Pat. No. 3,114,737 discloses that certain fluorenyl metallocenes are useful as catalysts for the aqueous polymerization of vinyl monomers such as styrene or acrylates. U.S. Pat. No. 4,892,851 also discloses a fluorenyl metallocene as a catalyst for polymerizing an olefin.

An object of the present invention is to provide new derivatives of fluorene. Another object of the present invention is to provide new methods for preparing fluorene derivatives.

Other aspects, objects, and advantages of the present invention will become apparent from the disclosure which follows.

SUMMARY OF THE INVENTION

In accordance with one aspect the present invention provides methods for preparing 1-methyl fluorene. Preferred embodiments involve converting fluoranthene to 1-methyl fluorene.

Another aspect of the invention involves methods for forming 4-methyl fluorene. Preferred embodiments involve converting phenanthrene to 4-methyl fluorene.

Still another aspect of the present invention provides a method for preparing tertiary butyl substituted fluorenes by reacting a carboxyl-substituted fluorene with trimethylaluminum.

Still another object of the present invention is to provide a number of new substituted fluorene compounds.

DETAILED DESCRIPTION OF THE INVENTION

Preparation of 1-methyl fluorene

Two different routes are available for preparing 1-methyl fluorene. In both cases a preferred embodiment involves preparing the 1-methyl fluorene from a starting material known as fluoranthene.

One of the routes involves ultimately reducing 1-hydroxymethyl fluorenone with hydrogen in the presence of a palladium carbon catalyst to produce 1-methyl fluorene. The other route involves ultimately reducing 1-hydroxymethyl fluorene with hydrogen in the presence of a palladium carbon catalyst to produce 1-methyl fluorene.

The reduction of the 1-hydroxymethyl fluorenone or the 1-hydroxymethyl fluorene with hydrogen can be carried out under any suitable reaction conditions. Generally, the reaction is carried out in the presence of a suitable liquid diluent, such as a solvent for the fluorene or fluorenone compound. Some examples of such liquids include benzene, toluene, xylene, tetrahydrofuran, or the like. Any suitable palladium carbon catalyst can be employed. Typically such catalysts would contain about 1 to about 20 wt. % palladium. The conditions of pressure and temperature can be readily selected by one skilled in the art for the optimum production. Typically, the reaction is conducted under conditions such that the hydrogen results in the total pressure being greater than atmospheric pressure. The resulting product can be recovered and purified using techniques of the type known in the art for separating such organic compounds.

The route involving the reduction of 1-hydroxylmethyl fluorenone allows one to produce 1-methyl fluorene from fluoranthene in three reaction steps. Specifically, the fluoranthene is reacted with hydrogen peroxide and acetic acid under suitable reaction conditions to produce 1-carboxylic acid fluorenone. The 1-carboxylic acid fluorenone is reduced using a "mixed hydride", i.e. lithium aluminum hydride/aluminum chloride catalyst to obtain the 1-methoxy fluorenone. The reduction using the lithium aluminum hydride/aluminum chloride catalyst is generally carried out in the presence of a suitable liquid diluent, typically a hydrocarbyl liquid or an ether such as diethyl ether and/or tetrahydrofuran.

The molar ratio of the lithium aluminum hydride to the aluminum chloride can vary over a wide range depending upon the particular results desired. Typically, the molar ratio of the lithium aluminum hydride to the aluminum chloride would be in the range of from about 3:1 to about 1:1. The "mixed hydride" catalyst is most generally used at a molar ratio of about 2:1 lithium aluminum hydride to aluminum trichloride.

The process for producing 1-methyl fluorene by the reduction of 1-hydroxymethyl fluorene involves four steps when one uses fluoranthene as the starting material. The first step involves the conversion of the fluoranthene to 1-carboxylic acid fluorenone, preferably by the reaction of the fluoranthene with hydrogen peroxide in acetic acid. The resulting 1-carboxylic acid fluorenone is then reduced with hydrogen using a palladium carbon catalyst in the same manner as previously described. The resulting 1-carboxylic acid fluorene is then reduced using a lithium aluminum hydride/aluminum chloride catalyst to obtain the 1-hydroxymethyl fluorene which is then reduced with hydrogen in the presence of a palladium carbon catalyst.

Preparation of 4-methyl fluorene

Two different routes are also available for preparing 4-methyl fluorene. One route involves reducing 4-hydroxymethyl fluorene with hydrogen in the presence of a palladium carbon catalyst. The other route involves reducing 1-hydroxymethyl fluorenone with hydrogen in the presence of a palladium carbon catalyst.

These reductions can be carried out in the same manner as described previously for the comparable reductions involved in preparing 1-methyl fluorene.

In a preferred embodiment the 4-methyl fluorene is prepared from phenanthrene. The phenanthrene is oxidized into 2,2'-dicarboxylic acid biphenyl by the use of hydrogen peroxide in acetic acid. The biphenyl product is then oxidized using sulfuric acid in the manner taught in J. Am. Chem. Soc. 64, 2845 (1942) to produce 4-carboxylic acid fluorenone. The 4-carboxylic acid fluorenone can then be reduced using the lithium aluminum hydride/aluminum chloride "mixed hydride" catalyst as described above to produce the 1-hydroxymethyl fluorenone which can be converted into the 4-methyl fluorene by reduction with hydrogen in the presence of a Pd carbon catalyst. In an alternate route, the 4-carboxylic acid fluorenone can be reduced with hydrogen in the presence of a palladium carbon catalyst to produce 4-carboxylic acid fluorene and that compound can be reduced with lithium aluminum hydride/aluminum chloride to produce 1-hydroxymethyl fluorene which in turn can then be reduced with hydrogen in the presence of a palladium carbon catalyst to yield the desired 4-methyl fluorene.

Preparation of tertiary butyl fluorene compounds

Tertiary butyl substituted fluorene compounds can be produced from carboxyl-substituted fluorene compounds by reacting the carboxy group with trimethylaluminum. The term "carboxyl-substituted fluorene compounds" as used herein is intended to refer to those fluorene compounds in which there is a substituent having a carbonyl radical in which the carbon of the carbonyl radical is bonded at some position on the fluorene ring. Examples include carboxylic acids and acetyls.

Typically this reaction involves dissolving the carbonyl-substituted fluorene in a suitable liquid and then adding a suitable amount of trimethylaluminum. The temperature and pressure conditions employed can vary over a wide range depending upon the results desired. It is currently preferred to carry out the reaction under reflux conditions for 1 to 20 hours, preferably 5 to 10 hours. The resulting product can be separated and purified using conventional techniques known in the art. The amount of trimethylaluminum employed can vary somewhat depending upon the particular fluorene compound that is used and the yield desired. Typically, when the fluorene compound is a carboxylic acid-substituted fluorene, it is generally desirable for the molar ratio of the trimethylaluminum to the fluorene compound to be at least about 5:1. On the other hand, when the fluorene compound is an acetyl compound, a molar ratio of only about 2:1 for the trimethylaluminum to the fluorene compound can be satisfactory.

A further understanding of the present invention will be provided by the following examples of some specific embodiments of the present invention.

EXAMPLE I

Preparation of 1-methyl fluorene

Two different reaction schemes have been used to prepare 1-methyl fluorene from fluoranthene. The reaction schemes can be illustrated by the following flow diagram. Both schemes involve the use of 1-carboxylic acid fluorenone as a starting material.

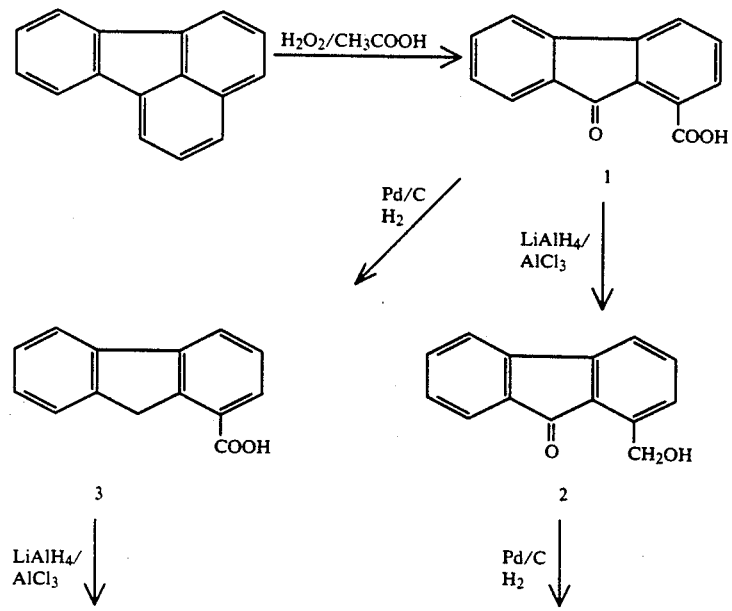

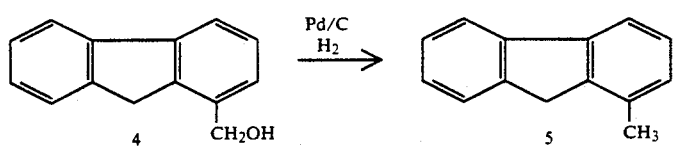

To prepare the 1-carboxylic acid fluoreneone, i.e. formula 1, 20.2 g (0.1m) of fluoranthene was dissolved in 150 ml of acetic acid at 90° C. At that temperature 200 ml of 30% aqueous H$_2$O$_2$, was then added gradually. Then the reaction mixture was stirred for another 3 hours at that temperature. At the beginning of the reaction, a light yellow precipitated was formed that disappeared after some time. Then the reaction mixture was cooled to 0° C. in an ice bath. An orange precipitate was formed and filtered off. The filtrate was poured into cold diluted aqueous HCl. An orange yellow precipitate was formed which was washed twice with H$_2$O and then dissolved in an aqueous NH$_3$ solution in order to remove the unreacted fluoranthene. Then the mixture was filtered. When the filtrate was neutralized with dilute HCl, an orange precipitate was formed. The precipitate, 1-carboxylic acid fluorenone, was filtered off and dried. The amount produced was 13.4 g.

Scheme I

About 0.76 g (0.02 mmol) of LiAlH$_4$ was suspended in a mixture of 75 ml of diethylether and 25 ml of tetrahydrofuran (dried over LiAlH$_4$). The mixture was cooled to 0° C. in an ice bath. Then 1.33 g (0.01 mmol) of AlCl$_3$ was added in small portions and the mixture was stirred at room temperature for 15 min. Then 4.2 g (0.02 mmol) of the carboxylic acid fluorenone dissolved in 400 ml of tetrahydrofuran was added via a dropping funnel while the reaction mixture was heated to reflux. Stirring was maintained for an additional 30 min. Then the reaction mixture was cooled to room temperature and the unreacted LiAlH$_4$ was destroyed with an aqueous solution of HCl. The organic phase was washed twice with water and dried over NaSO$_4$. The the solvent was removed by an evaporator. The solid, i.e. 1-hydroxymethyl fluorenone (formula 2), was recovered in the amount of 3.2 g.

The raw 1-hydroxymethyl fluorenone can be used without further purification. 2 g of palladium on carbon catalyst containing about 10 weight percent Pd was weighed into a flask and 4.2 g (0.02 mmol) of the recovered 1-hydroxymethyl fluorenone was dissolved in 250 ml tetrahydrofuran and added to the flask. The hydrogenation was conducted at room temperature with a slight overpressure of H$_2$ until 1350 ml of H$_2$ was consumed. The reaction mixture was filtered and the solvent of the filtrate was removed in vacuo. The creme colored residue was extracted with pentane, the solution was filtered over silica gel, and the solvent removed in vacuo. The resulting product, 1-methyl fluorene, was a colorless solid and formed in quantitative yield.

Scheme II

In the second route, the 1-carboxylic acid fluorenone is reduced using the palladium carbon catalyst in the same manner as described for converting the 1-hydroxymethyl fluorenone to 1-methyl fluorene. A quantitative yield of 1-carboxylic acid fluorene, i.e. formula 3, was obtained. The volume of hydrogen consumed was 960 ml. This product was then reduced to 1-hydroxymethyl fluorene, i.e. formula 4, by using the LiAlH$_4$/AlCl$_3$ "mixed hydride" catalyst as described for the production of the 1-hydroxymethyl fluorenone. The 1-hydroxymethyl fluorene was then reduced using the palladium carbon catalyst and hydrogen to yield 1-methyl fluorene.

EXAMPLE II

Preparation of 1-tert-butyl fluorene

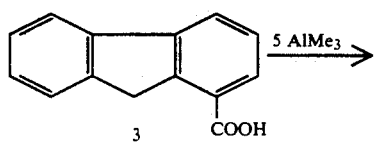

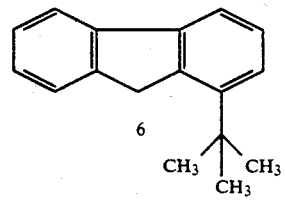

About Z g (0.01 mmol) of 1-carboxylic acid fluorene was suspended in 50 ml of toluene. Then 4.6 ml, i.e. about 0.05 mole of AlMe$_3$ was added to the solution and the reaction mixture was refluxed for 10 hours. Upon heating, the reaction mixture formed a homogeneous solution. The reaction mixture was cooled to room temperature and then poured into ice cooled diluted aqueous HCl. The organic layer was separated, washed with H$_2$O, and dried over Na$_2$SO$_4$. Then the solvent was removed in vacuo. The colorless residue was extracted with pentane, the solution filtered over silica, and the solvent removed in vacuo. The yield of 1-tert-butyl fluorene, formula 6, was quantitative.

EXAMPLE III

Preparation of 2-tert-butyl fluorene

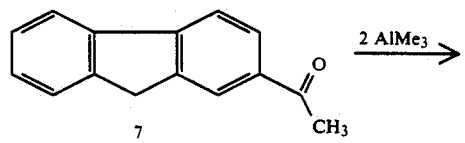

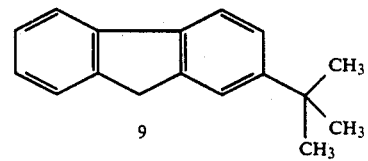

In this reaction 2-acetyl fluorene was reacted with trimethyl aluminum. The methylation was analogous to the conversion of compound 3 to compound 6 described in Example II. However, in this case, only a two-fold excess of AlMe$_3$, was necessary. The 2-tert-butyl fluorene was formed as a white solid in quantitative yield.

EXAMPLE IV

Preparation of 4-methyl fluorene

Two different reaction schemes have been used to prepare 4-methyl fluorene, i.e. formula 15. The schemes can be summarized as follows.

Scheme 1

The compound of formula 11 was reduced using LiAlH$_4$ and AlCl$_3$ in the same manner as in Example I. The reaction produced an 80% yield of 4-hydroxymethyl fluorenone, i.e. formula 14, which was then reduced using hydrogen and the palladium/carbon catalyst previously described. A quantitative yield of 4-methyl fluorene resulted.

Scheme 2

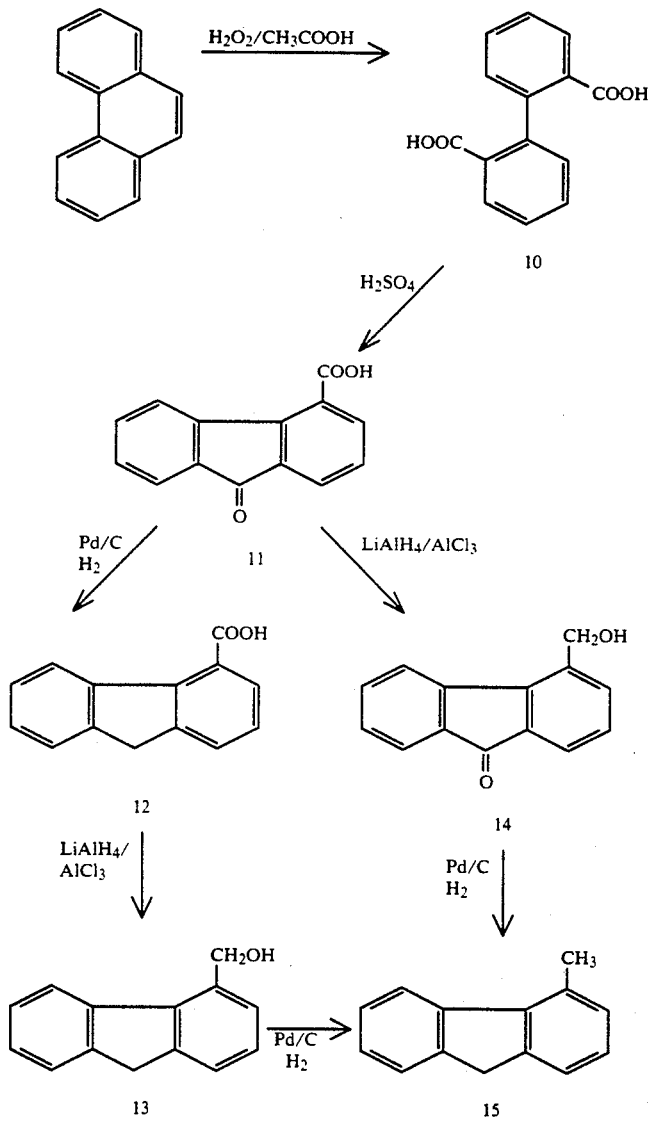

Both schemes require 4-carboxylic acid fluorenone, formula 11, as a starting material. This compound was produced from phenanthrene using a procedure similar to that disclosed in J. Org. Chem. 21. 243 (1956) except that no acetic anhydride was used. Instead, hydrogen peroxide and acetic acid were used to obtain a 67% yield of 2,2'-dicarboxylic acid biphenyl, i.e. formula 10.

The biphenyl product of formula 10 was then oxidized using sulfuric acid in the manner taught in J. Am. Chem. Soc. 64. 2845 (1942) to obtain an 82% yield of 4-carboxylic acid fluorenone, i.e. formula 11.

The compound of formula 11 was reduced using hydrogen and the palladium carbon catalyst described previously. The reaction produced a quantitative yield of 4-carboxylic acid fluorene, i.e. formula 12. Reduction of this acid with LiAlH$_4$ and AlCl$_3$ resulted in an 80% yield of 4-hydroxymethyl fluorene, i.e. formula 13. This product was then reduced using hydrogen and the palladium carbon catalyst to produce a quantitative yield of 4-methyl fluorene.

Example V

Preparation of 4-tert-butyl fluorene 4-carboxylic acid fluorene was reacted with trimethylaluminum generally as described in Example II to produce a 60% yield of 4-tert-butyl fluorene.

That which is claimed is:

1. A method for preparing 1- methyl fluorene from fluoranthene comprising reacting fluoranthene with $H_2O_2$ and acetic acid under suitable conditions to produce 1-carboxylic acid fluorenone, then reacting said 1-carboxylic acid fluorenone with $LiAlH_4$ and $AlCl_3$ under suitable reaction conditions to produce 1- hydroxymethyl fluorenone, and then reducing said 1-hydroxymethyl fluorenone with hydrogen in the presence of a palladium carbon catalyst under suitable conditions to produce said 1- methyl fluorene.

2. A method for preparing 1-methyl fluorene from fluoranthene comprising reacting said fluoranthene with $H_2O_2$ and acetic acid under suitable conditions to produce 1- carboxylic acid fluorenone, then reacting said 1- carboxylic acid fluorenone with hydrogen in the presence of a palladium carbon catalyst under suitable conditions to produce 1-carboxylic acid fluorene, and then reacting said 1-carboxylic acid fluorene with $LiAlH_4$ and $AlCl_3$ under suitable conditions to produce 1-hydroxymethyl fluorene, and then reacting said 1-hydroxymethyl fluorene with hydrogen in the presence of a palladium catalyst to yield said 1-methyl fluorene.

3. A method for producing 4-methyl fluorene from phenathrene comprising reacting $H_2O_2$ and acetic acid with phenanthrene under suitable conditions to produce 2,2'-dicarboxylic acid biphenyl, then reacting said 2,2'-dicarboxylic acid biphenyl with sulfuric acid under suitable conditions to produce 4-carboxylic acid fluorenone, then reacting said 4-carboxylic acid fluorenone with hydrogen in the presence of a carbon palladium catalyst under suitable conditions to produce 4-carboxylic acid fluorene, and then reacting said 4-carboxylic acid fluorene with $LiAlH_4$ and $AlCl_3$ to yield 4-hydroxymethyl fluorene, and then reducing said 4-hydroxymethyl fluorene with hydrogen in the presence of a palladium carbon catalyst to yield said 4-methyl fluorene.

4. A method for preparing 4-methyl fluorene from phenathrene comprising reacting $H_2O_2$ and acetic acid with phenathrene under suitable conditions to produce 2,2'-dicarboxylic acid biphenyl, then reacting said 2,2'-dicarboxylic acid biphenyl with sulfuric acid to produce 4-carboxylic acid fluoreneone, then reacting said 4-carboxylic acid fluorenone with $LiAlH_4$ and $AlCl_3$ to produce 4-hydroxymethyl fluorenone, and then reducing said 4-hydroxymethyl fluorenone with hydrogen in the presence of a palladium carbon catalyst to produce said 4-methyl fluorene.

5. A method for preparing 1-tertiary butyl fluorene comprising reacting fluoranthene with hydrogen peroxide and acetic acid under suitable conditions to produce 1-carboxylic acid fluorenone and then reducing said 1-carboxylic acid fluorenone with hydrogen in the presence of a palladium carbon catalyst to produce 1-carboxylic acid fluorene and then reacting said 1-carboxylic acid fluorene with trimethylaluminum under suitable conditions to yield said 1-tert-butyl fluorene.

6. The compound known as 1-tert-butyl fluorene.

7. A method for preparing 4-tert-butyl fluorene comprising reacting 4-carboxylic acid fluorenone with hydrogen in the presence of a carbon palladium catalyst under suitable conditions to produce 4-carboxylic acid fluorene and then reacting said 4-carboxylic acid fluorene with trimethylaluminum under suitable conditions to yield said 4-tert-butyl fluorene.

8. The compound 4-tert-butyl fluorene.

* * * * *